United States Patent
Strande et al.

(10) Patent No.: US 10,564,093 B2
(45) Date of Patent: Feb. 18, 2020

(54) SINGLE INJECTION COMPETITION ASSAYS

(71) Applicant: Molecular Devices, LLC, San Jose, CA (US)

(72) Inventors: Christopher Iver Strande, Edmond, OK (US); Aaron David Martin, Oklahoma City, OK (US)

(73) Assignee: Molecular Devices, LLC, San Jose, CA (US)

( * ) Notice: Subject to any disclaimer, the term of this patent is extended or adjusted under 35 U.S.C. 154(b) by 3 days.

(21) Appl. No.: 15/737,658

(22) PCT Filed: Jul. 11, 2016

(86) PCT No.: PCT/US2016/041788
§ 371 (c)(1),
(2) Date: Dec. 18, 2017

(87) PCT Pub. No.: WO2017/011404
PCT Pub. Date: Jan. 19, 2017

(65) Prior Publication Data
US 2018/0195954 A1    Jul. 12, 2018

Related U.S. Application Data

(60) Provisional application No. 62/191,151, filed on Jul. 10, 2015.

(51) Int. Cl.
| | | |
|---|---|---|
| G01N 33/557 | (2006.01) |
| G01N 21/27 | (2006.01) |
| G01N 21/552 | (2014.01) |
| G01N 33/543 | (2006.01) |
| G01N 33/53 | (2006.01) |
| G01N 35/08 | (2006.01) |

(Continued)

(52) U.S. Cl.
CPC ......... *G01N 21/272* (2013.01); *G01N 21/553* (2013.01); *G01N 33/5306* (2013.01); *G01N 33/54306* (2013.01); *G01N 35/08* (2013.01); *B01L 2300/0636* (2013.01); *G01N 2021/0346* (2013.01); *G01N 2021/058* (2013.01)

(58) Field of Classification Search
None
See application file for complete search history.

(56) References Cited

U.S. PATENT DOCUMENTS

| | | |
|---|---|---|
| 2005/0019933 A1 | 1/2005 | Andersson et al. |
| 2011/0295512 A1 | 12/2011 | Quinn |

(Continued)

FOREIGN PATENT DOCUMENTS

JP    2010-008113    1/2010

OTHER PUBLICATIONS

International Search Report and Written Opinion of the International Searching Authority dated Sep. 26, 2016 filed in related application PCT/US2016/041788.

(Continued)

*Primary Examiner* — Christopher L Chin
(74) *Attorney, Agent, or Firm* — McAfee & Taft

(57) ABSTRACT

Disclosed is a method for preparing dispersion gradients and an SPR injection method for determining full kinetics and affinity analysis in the presence of a competitor molecule. The SPR injection provides a dispersion gradient of two or more samples to a SPR flow cell and detector.

6 Claims, 15 Drawing Sheets

(51) Int. Cl.
*G01N 21/03* (2006.01)
*G01N 21/05* (2006.01)

(56) References Cited

U.S. PATENT DOCUMENTS

2013/0157251 A1    6/2013   Quinn et al.
2013/0273564 A1   10/2013   Quinn

OTHER PUBLICATIONS

Jordan L. Woehl, et al., The Extracellular Adherence Protein from *Staphylococcus aureus* Inhibits the Classical and Lectin Pathways of Complement by Blocking Formation of the C3 Proconvertase, The Journal of Immunology, vol. 193, No. 12, Nov. 7, 2014, pp. 6161-6171.

European Search Report dated Nov. 8, 2018 received in related application 16825000.9, pp. 1-12.

Office Action and Translation of "Notice of Reasons for Rejection" dated Jan. 25, 2019, Patent Application No. JP 2017-568357.

Current Invention

SINGLE INJECTION COMPETITION ASSAYS

CROSS REFERENCE TO RELATED APPLICATION

This application claims the benefit of U.S. Provisional Application No. 62/191,151 filed Jul. 10, 2015

BACKGROUND

Biosensors are commonly used to perform kinetic studies of complex molecular interactions such as those between drug-target, hormone-receptor, enzyme-substrate and antigen-antibody. The biosensors are typically in a flow injection-based fluidic system wherein one or more sensing regions are housed within a flow cell conduit of the fluidic system. The fluidic system further defines one or more flow channel conduits that direct fluid flow to the sensing regions in the flow cell conduit. The sensing region provides surfaces that support immobilized molecules referred to generally as "ligands." The ligands are potential binding partners for molecules known as "analytes" which are present in fluids that are directed to the sensing region of the flow cell conduit via the flow channel conduit. Typically, one member of an affinity pair, the ligand, is immobilized onto a surface in the sensing region while the second member, the analyte, is exposed to this ligand-coated surface for sufficient time to form analyte-ligand complexes at the sensing region.

Competition assays provide the ability to find active site binders directly by competing fragment hits with a control molecule. Such assays are commonly performed using surface plasmon resonance (SPR). However, competition assays typically require multiple steps in order to determine full kinetic and affinity data for the competing molecules. As a result analysis is time consuming and costly.

SUMMARY

Disclosed herein is a single SPR injection method for determining full kinetics and affinity analysis in the presence of a competitor molecule. The single SPR injection provides a dispersion gradient of two or more samples to a SPR flow cell and detector.

In part, this disclosure provides a method for performing an injection of a dispersion gradient for analysis by a sensor. The method provides for pulling a first sample containing one or more analytes into a sample holding line followed by pulling a second sample containing one or more analytes into a sample holding line thereby forming a dispersion gradient of said first sample and said second sample. Subsequently, the method pushes the dispersion gradient through a flow line to the sensor.

Additionally, this disclosure provides a method for performing competitive binding analysis of two analytes. The method prepares a control sample of a first analyte by pulling a first volume of said first analyte into a sample holding line, pulling a second volume of said first analyte into said sample holding line. The control sample is injected through an SPR sensor within which is a bound ligand. As the control sample passes through the SPR sensor measurements are taken of the binding interaction of the first analyte in the control sample with said ligand using SPR analysis to generate a binding interaction curve. The method also prepares a binding competitive analysis dispersion gradient by pulling a sample comprising the first analyte and a second analyte into the sample holding line, followed by pulling a sample of the first analyte into the sample holding line thereby forming the binding competitive analysis dispersion gradient. Following preparation of the binding competitive analysis dispersion gradient, the method provides for pushing the resulting competitive analysis dispersion gradient through said SPR sensor and measuring the binding interaction of the competitive analysis dispersion gradient with said ligand to generating a binding interaction curve. The binding interaction curve generated by control sample is subtracted from the binding interaction curve generated by the competitive analysis dispersion gradient to determine the competitive binding the second analyte to the ligand in the presence of the first analyte.

DETAILED DESCRIPTION

Figure 1:
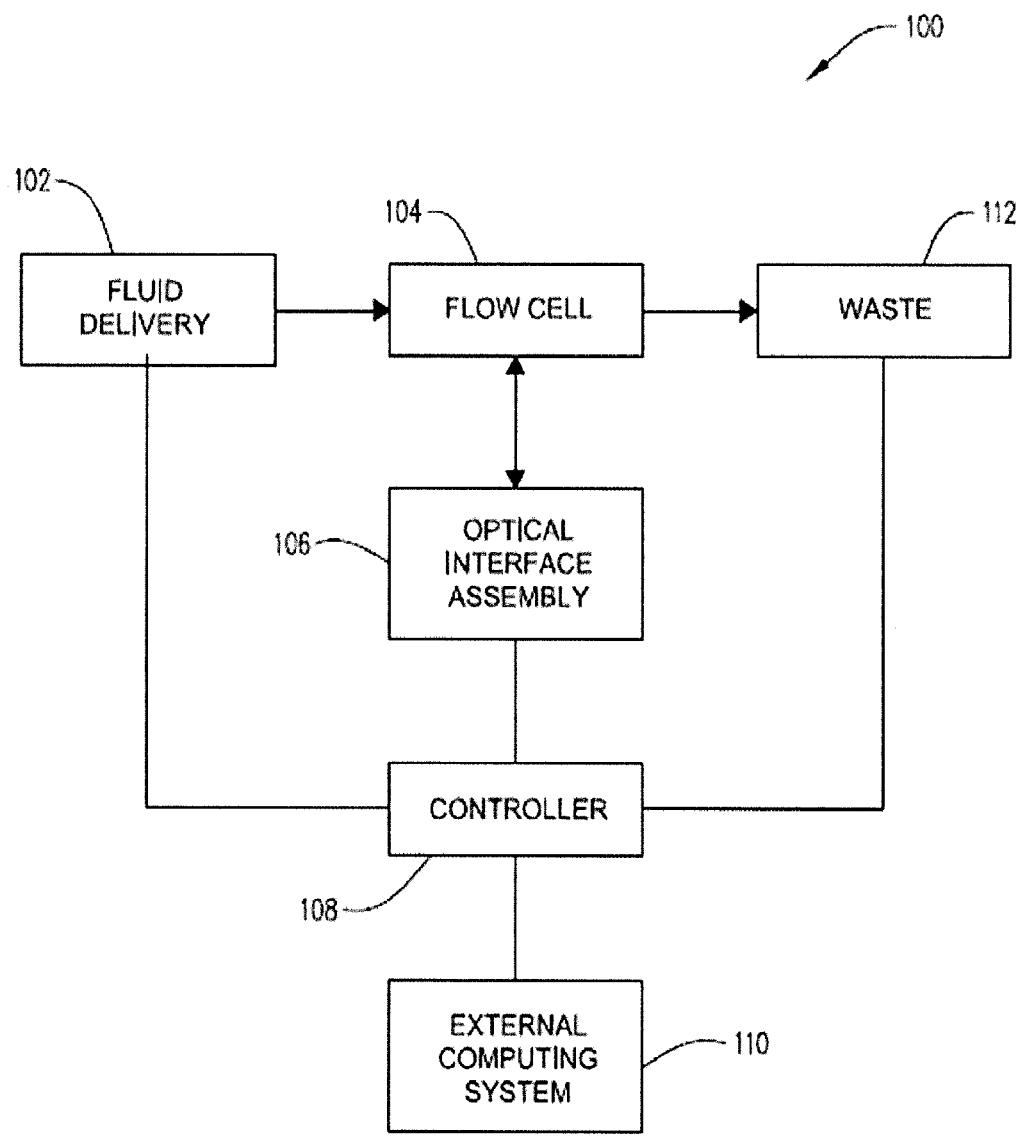
FIG. 1 is a diagram of an SPR test system, which can use the fluid delivery system of some embodiments.

SPR techniques are well known to those skilled in the art and will not be discussed in detail herein. The following disclosure will focus on the novel approach of generating gradient profiles of two or more analytes in a single injection and performing competitive analysis of two or more analytes using the improved method for generating dispersion gradients. Dispersion gradient may be analyzed using flow-injection based sensing systems. For the purposes of this disclosure, the analysis of the dispersion gradients will be described in terms of Surface Plasmon Resonance (SPR). In flow-injection based sensing systems, typically used for biomolecular interaction analysis applications, a sample containing at least analyte flows across a surface sensitive detector through flow injection. In this instance, the sample flows through a SPR cell housing the SPR sensing surface.

In the description that follows, like parts are marked throughout the specification and drawings with the same reference numerals, respectively. The drawings are not necessarily to scale and the proportions of certain parts have been exaggerated to better illustrate details and features of the invention. The terms "inwardly" and "outwardly" are directions toward and away from, respectively, the geometric axis of a referenced object. Where components of relatively well-known design are employed, their structure and operation will not be described in detail.

Referring now to FIG. 1, a diagram of an SPR testing system 100 is illustrated. A flow injection system or fluid delivery system 102 includes a complex of flow channels, valves, pumps and/or other components configured to provide a substantially constant flow of fluid from a plurality of fluid sources to a flow cell 104. According to embodiments, the flow cell 104 may be operatively coupled to an optical interface assembly 106, which is configured to carry out an SPR measurement. SPR optical interface assemblies are known in the art and may include a thin-film optical substrate, prism, illuminator and detector.

Typically, the flow cell may be configured to maintain an electro-optical relationship between the SPR coupling surface and a plurality of active sensing regions (not shown). The thin-film optical substrate is typically derivatized to possess a coating that enables biomolecules ("ligands") to be immobilized to the substrate. The immobilized biomolecules usually possess binding specificity for one or more particular polypeptides, proteins, polynucleotides, kinases, and/or other small molecules. The areas of specific affinity may be referred to as active sensing regions. The active sensing regions may generally be separated by one or more continuous areas resistant to non-specific binding of one or more of the above. Experimental design typically designates one or more active sensing regions as reference sensing regions by not immobilizing a biomolecule to the corresponding region of interrogation on the thin-film optical substrate.

The active sensing regions include binding moieties such as anchored proteins that extend upward from the surface of the thin-film optical substrate into the fluid in and flowing through the flow cell 104. If an analyte flowing through the flow cell includes a particular molecule or biomolecule for which the binding moiety of a particular active sensing region has affinity, the molecule or biomolecule may bind to or associate with the binding moiety according to a characteristic association kinetic. Association of the molecule or biomolecule to the active sensing region changes the index of refraction in a volume near the active sensing region. Typically, the analyte is made to pass through the flow cell as a homogenous volume segment of constant or fixed concentration. However, there are other methods known in the art where the analyte volume segment is made to undergo dispersion with either the buffer solution or a third solution en route to the flow cell in order to present a gradient in analyte concentration to the active sensing regions. See for example, U.S. Patent Publication 2011/0295512 and U.S. Patent Publication 2013/0273564.

If another sample containing analyte or buffer solution is then flowed through the flow cell, and the other analyte or buffer does not include the particular molecule or biomolecule, the bound molecule or biomolecule may dissociate from the binding moiety of the active sensing region according to a characteristic dissociation kinetic. The buffer is typically a solution of near neutral pH or a weak acid or weak base, which contains no analyte. Suitable buffers are typically saline solutions containing HEPES, phosphate, TRIS and/or other additives depending on the desired experimental conditions.

Dissociation of the molecule or biomolecule from the active sensing region again changes the index of refraction of the fluid volume near the active sensing region. Generally, complete dissociation may reduce the index of refraction to at or near the starting index of refraction before the initial binding. In some cases, complete dissociation may take a very long time and/or the index of refraction may not quite return to its original value. Moreover, a series of associations and dissociations may result in a gradual change in the index of refraction. When the change becomes too great, the surface of the thin-film optical substrate may need to be conditioned or regenerated to return substantially to its initial state.

In circumstances where the sensing surface needs to be regenerated, regeneration can be performed by flowing a wash fluid, such as water, a detergent, and/or an acid for example, through the flow cell. Such regeneration may generally return the index of refraction near the active sensing region to near its original value. For example, during a regeneration phase, water, a detergent, an acid, or sequential combinations of water, detergent, and acid may be injected into the flow cell to remove the last tenacious bits of the molecule or biomolecule that remain adhered to the active sensing region after conclusion of the dissociation.

An optical interface assembly 106 is operable to illuminate the thin-film optical substrate and detect variations in the amount of reflected light energy. The amount of reflected light energy is, in turn, affected by binding (or not) of a molecule or biomolecule from an analyte onto the active sensing regions.

As discussed above, the optical interface assembly 106 typically includes an illuminator configured to illuminate the thin-film optical substrate. The illuminator may include a number of discrete and/or integrated components operative to produce the illumination. Typically, a prism is aligned to receive light from the illuminator and couple it to the thin-film optical substrate. A portion of the photons of light may be converted to surface plasmons. In some SPR systems, the remaining photons are reflected from the thin-film optical substrate, and the prism is configured to couple them out to a detector. The detector is operable to detect variations in the proportion of photons reflected from across the surface of the thin-film optical substrate, the variations typically include a component related to the association and dissociation of molecular and/or biomolecular moieties from the analyte onto one or more of the active sensing regions. Typically, higher loading (i.e., a greater proportion of binding moiety active sites being associated with the specific molecule or biomolecule) tends to increase the conversion of photons to surface plasmons (and hence reduce the number of reflected photons), and lower loading tends to minimize the conversion of photons to surface plasmons (and hence maximize the number of reflected photons).

Other SPR systems detect a shift in the emission angle of the plasmons by tracking the SPR dip minimum. Higher loadings of analyte results in increasing the angle at which emission occurs.

A controller 108 may be operatively coupled to the fluid delivery system 102 and optical interface assembly 106, and may include an interface to an external computing system or network 110. Alternatively, the interface to the external computing system or network 110 may be omitted and the apparatus 100 may operate as a stand-alone system. Controller 108 may be used to control the output of the illuminator, perform image processing on the image acquired by the detector, perform data analysis or transmit image data to an external processor 110 for image processing, transmit and receive status and command data to and from internal components and external systems, provide a human interface via a keyboard, display, and/or other status indicators (not shown), and control the fluid delivery system 102. In particular, the fluid delivery system may include pumps and valves with electrical control interfaces, and the controller 108 may transmit signals to operate the pumps, valves, etc. of the fluid delivery system 102. As necessary, the controller 108 may be operatively coupled to waste system 112.

Figure 2:
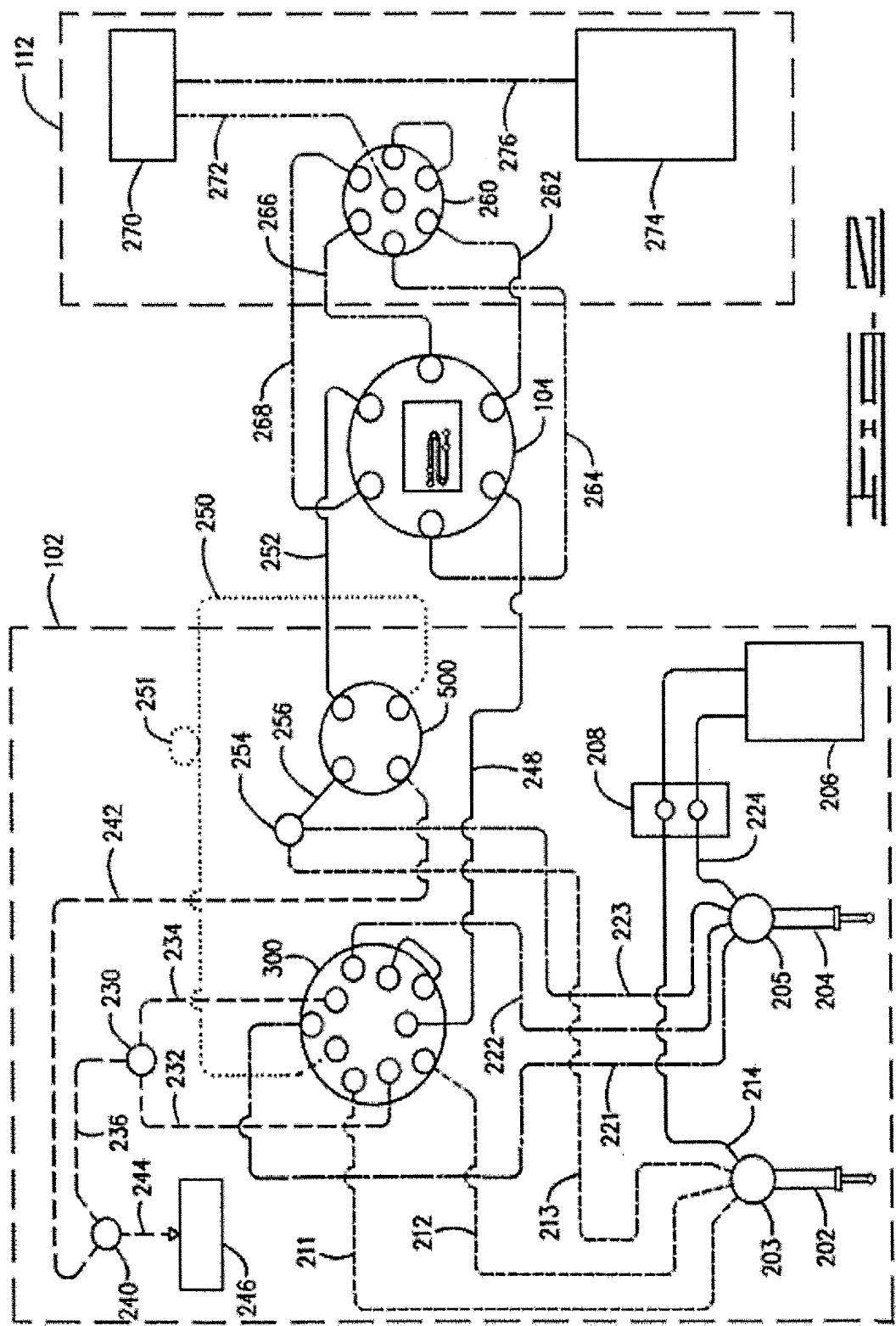
FIG. 2 schematically depicts one configuration of a system suitable for practicing the methods disclosed herein.

The system of FIG. 2 is a schematic diagram of a fluid delivery system 102, a flow cell 104 and waste system 112 according to some embodiments. The fluid delivery system 102 includes a first pump 202, and a second pump 204 configured to pump fluids through the flow cell 104 via first multi-port valve 300 and second multi-port valve 500. The first and second pumps 202, 204 may each be a pump such as a syringe pump, such as the Cavro XLP6000 syringe pump or Cavro Centris syringe pump marketed by Tecan. Each pump 202, 204 has a distribution valve 203, 205 so as to be configured to pump to or from one of four flow lines. Generally, the distribution valve 203 can be set for first pump 202 to pump buffer solution into the pump's syringe from buffer storage 206 through flow line 214 and out through one of flow lines 211, 212 and 213. Accordingly, distribution valve 203 is configured such that one port of first multi-port valve 300 or second multi-port valve 500 receives fluid from pump 202 at any time. The buffer solution from buffer storage 206 can pass through a degasser 208 prior to being introduced into first pump 202.

Similarly, distribution valve 205 typical can be set for second pump 204 to pump buffer solution into the pump's syringe from buffer storage 206 through flow line 224 and out through one of flow lines 221, 222, 223. Accordingly, distribution valve 205 is configured such that one port of first multi-port valve 300 or second multi-port valve 500 receives fluid from pump 204 at any time. Again, buffer solution from buffer storage 206 can pass through a degasser 208 prior to being introduced into second pump 204. Any suitable distribution valve can be utilized for distribution valve 203, 205.

Flow lines 211 and 212 connect first pump 202 in fluid flow communication to first multi-port valve 300. Flow lines 221 and 222 connect second pump 204 in fluid flow communication to first multi-port valve 300. Additionally, first multi-port valve 300 is connected to a junction 230 via flow lines 232 and 234. Junction 230 is also connected to flow line 236, which places junction 230 in fluid flow communication with junction 240. Junction 240 is operably connected to probe 244, which can obtain samples from sample rack 246 or can be placed in fluid flow communication with wash station 270. Additionally, junction 240 is in fluid flow communication with second multi-port valve 500 via flow line 242. Thus, fluid flow across junction 240 is either between probe 244 and second multi-port valve 500 via flow line 242 or is between probe 244 and junction 230 via flow line 236, depending on the pump 202, 204 in operation and its associated distribution valve setting. In turn, fluid flow across junction 230 is between probe 244 and first multi-port valve 300 either by flow line 232 or by flow line 234, depending on the pump 202, 204 in operation and its associated distribution valve setting. Accordingly, first multi-port valve 300 can receive fluid, typically samples, from probe 244 either through flow line 232 or through flow line 234. Additionally, probe 244 can receive fluid, typically buffer solution, from first multi-port valve 300 through either flow line 232 or through flow line 234. Finally, first multi-port valve 300 is in fluid flow communication with flow cell 104 via line 248, which places it in communication with waste selector 260.

Flow line 213 connects first pump 202 in fluid flow communication with junction 254, which is in fluid flow communication with second multi-port valve 500 via flow line 256. Similarly, flow line 223 connects second pump 202 in fluid flow communication with junction 254; hence, to second multi-port valve 500 via flow line 256. Thus, fluid flow across junction 254 is either between first pump 202 and second multi-port valve 500 via flow lines 213 and 256 or is between second pump 204 and second multi-port valve 500 via flow lines 223 and 256, or both pumps 202, 204 depending on which pump(s) is in operation and its associated valve setting.

As mentioned above, second multi-port valve 500 can be in fluid flow communication with probe 244 via flow line 242. Additionally, second multi-port valve 500 is in fluid flow communication with first multi-port valve 300 via flow line 250 and with flow cell 104 via flow line 252. Flow line 250 can include dispersion loop 251. Fluids entering flow cell 104 through flow line 252 interact with the thin-film optical substrate of the optical interface assembly 106. It should be noted that fluids entering flow cell 104 through flow line 248 can also interact with the optical interface depending on the selection of the waste port.

Flow cell 104 is connected in fluid flow communication with waste selector 260 via flow lines 262, 264, 266 and 268. Hence, fluid entering through flow line 248 or flow line 252 is delivered to waste selector 260. Waste selector 260 is in turn in fluid flow communication with wash station 270 via flow line 272. Wash station 270 is also in fluid flow communication with waste storage 274 via flow line 276.

Figure 3:
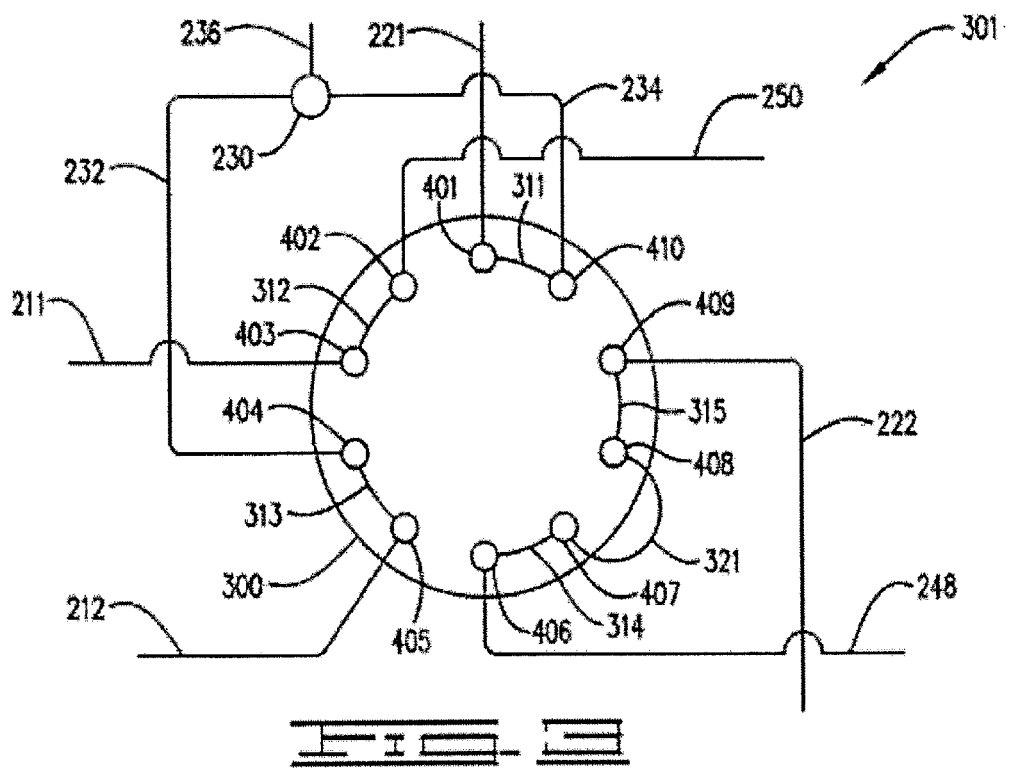
FIG. 3 is a schematic diagram of a first position of the ten-port valve used in FIG. 2

According to one embodiment, first multi-port valve 300 can be a two-position, ten-port valve as shown or can be a two-position, eight-port valve; thus eliminating jumper flow line 321 described below. FIG. 3 is a diagram of first multi-port valve 300 in a position A or first position 301. The valve position 301 couples five pairs of ports. Port 401 is coupled via a flow channel 311 to port 410; port 402 is coupled via a flow channel 312 to port 403; port 404 is coupled via a flow channel 313 to port 405; port 406 is coupled via a flow channel 314 to port 407; and port 408 is coupled via a flow channel 315 to port 409. Additionally, port 408 is coupled to port 407 via a flow line 321. In abbreviated form, the following ports are linked in the first position 301: 401-410, 402-403, 404-405, 406-407, 408-409.

In first position 301, a fluid in flow line 211, which acts as a holding line, can be pushed by first pump 202 through the first multi-port valve 300. The fluid enters at port 403 and exits at port 402. The fluid is then pushed to second multi-port valve 500 via flow line 250. Additionally, a fluid can be pulled into flow line 221, which acts as a holding line, by second pump 204. The fluid is pulled into probe 244 and through flow line 236 and 234 to enter first multi-port valve 300 via port 410 and exit via port 401. From port 401, the fluid is introduced into holding line 221. For example, the fluids may include analytes. Additionally, buffer fluid can be pushed through first multi-port valve 300, as further described below.

Figure 4:
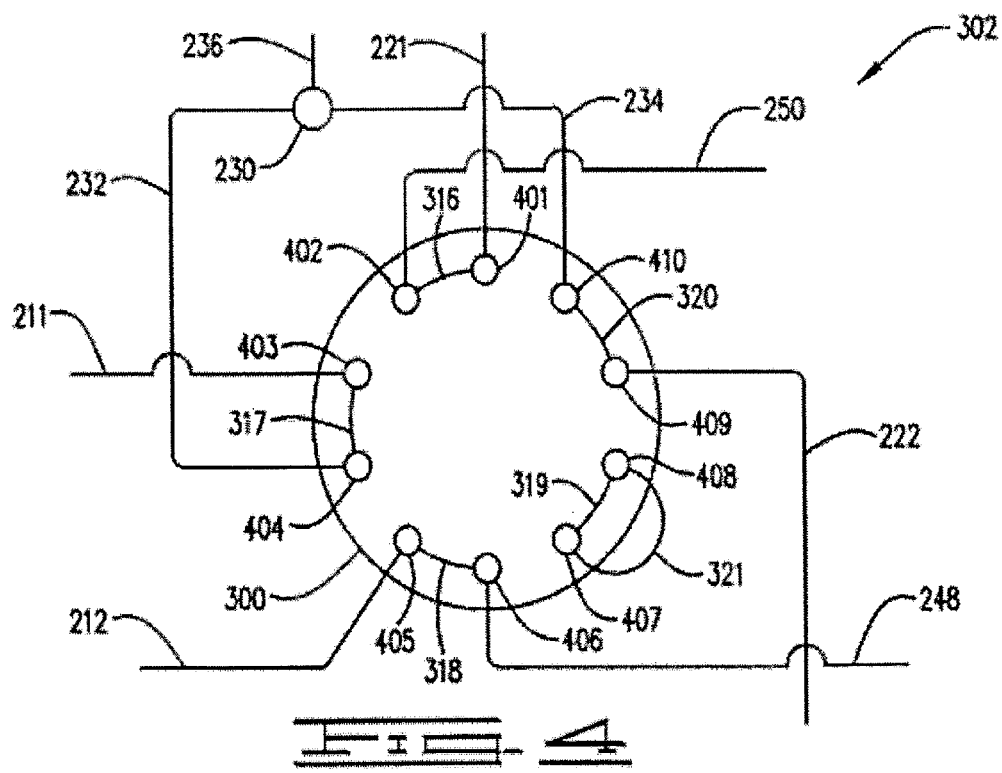
FIG. 4 is a schematic diagram of a second position of the ten-port valve used in FIG. 2.

FIG. 4 is a diagram of first multi-port valve 300 in a position B or second position 302. The valve position 302 couples five pairs of ports. Port 401 is coupled via a flow channel 316 to port 402; port 403 is coupled via a flow channel 317 to port 404; port 405 is coupled via a flow channel 318 to port 406; port 407 is coupled via a flow channel 319 to port 408; and port 409 is coupled via a flow channel 320 to port 410. As in first position 301, port 408 is coupled to port 407 via a flow line 321. In abbreviated form, the following ports are linked in second position 302: 401-402, 403-404, 405-406, 407-408, 409-410.

In second position 302, a fluid in holding line 221 can be pushed by second pump 204 through the first multi-port valve 300. The fluid enters at port 401 and exits at port 402. The fluid is then pushed to second multi-port valve 500 via flow line 250. Additionally, a fluid can be pulled into holding line 211 by first pump 202. The fluid is pulled into probe 244 and through flow line 236 and 232 to enter first multi-port valve 300 via port 404 and exit via port 403. From port 403, the fluid is introduced into holding line 211. For example, the fluids may include analytes. Additionally, buffer fluid can be pushed through first multi-port valve 300, as further described below.

In the above, multi-port valve 330 is described as having ten channels; however, other configurations will be readily apparent, such as the valve can operate so that one channel serves for two different positions. For example, the valve can be built such that the flow channels are five slots on a rotating head, and a motor rotates the head between two positions. Accordingly, there would only be five channels with each channel having a first position connecting a first and a second port, and a second position connection the second port and a third port.

Figure 5:
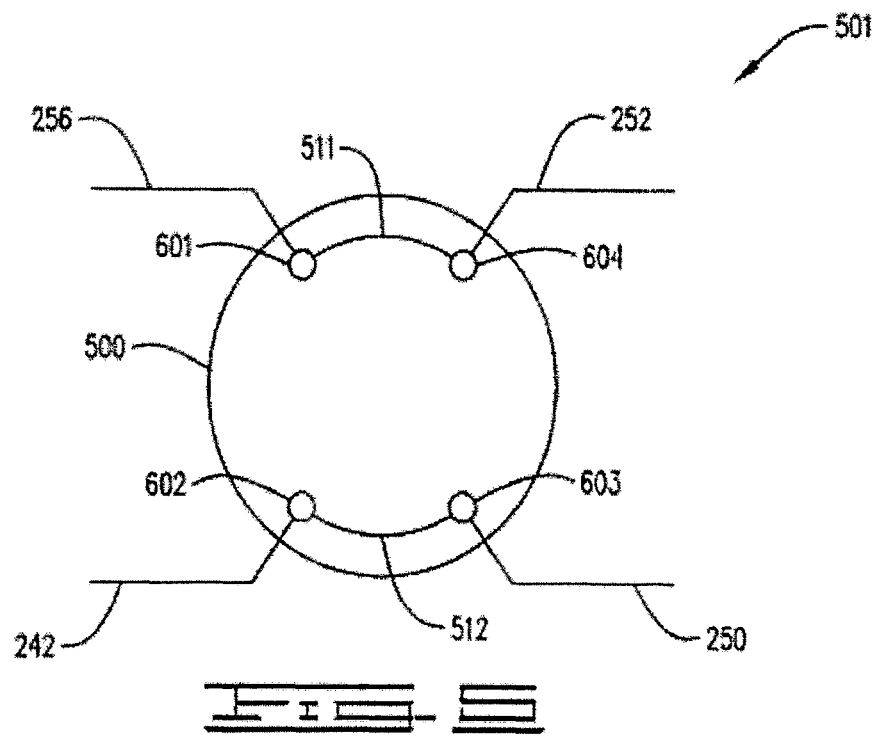
FIG. 5 is a schematic diagram of a first position of the four-port valve used in FIG. 2.
Figure 6:
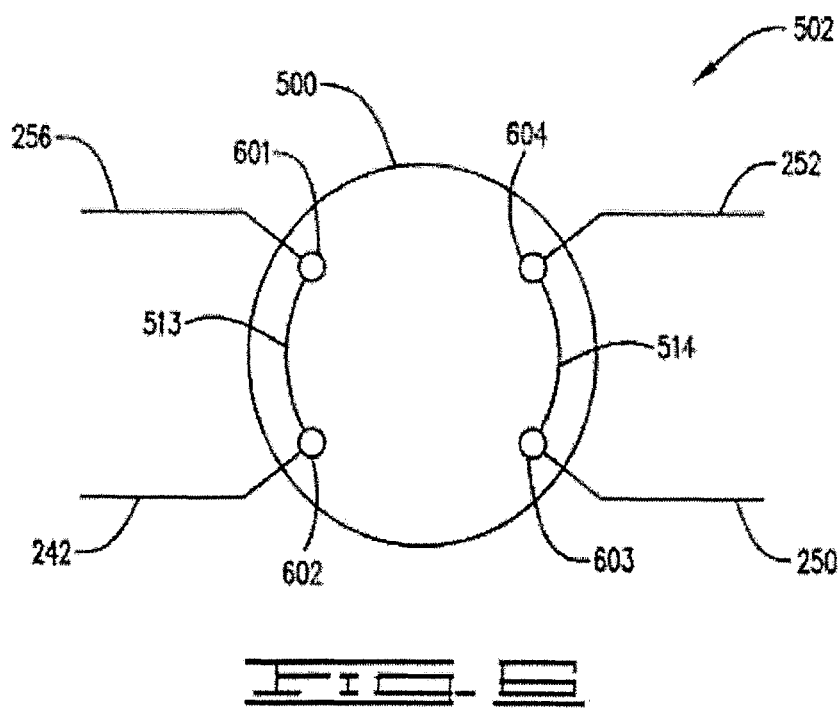
FIG. 6 is a schematic diagram of a second position of the four-port valve used in FIG. 2.

According to some embodiments, second multi-port valve 500 can be a two-position, four-port valve as shown. FIG. 5 is a diagram of second multi-port valve 500 in a position A or first position 501. The valve position 501 couples two pairs of ports. Port 601 is coupled via a flow channel 511 to port 604; and port 602 is coupled via a flow channel 512 to port 603. In abbreviated form, the following ports are linked in first position 501: 601-604, 602-603.

In first position 501, a buffer fluid introduced into flow line 213 or flow line 223 can be pushed by first pump 202 or second pump 204, respectively, through flow line 256 and into second multi-port valve 500. The fluid enters at port 601 and exits at port 604 to be introduced into flow cell 104 via flow line 252. The fluid can then be pushed to waste system 112. Typically, the fluid will be a buffer fluid for cleaning and for dissociation in flow cell 104.

FIG. 5 is a diagram of second multi-port valve 500 in a position B or second position 502. The valve position 502 couples two pairs of ports. Port 601 is coupled via a flow channel 513 to port 602; and port 603 is coupled via a flow channel 514 to port 604. In abbreviated form, the following ports are linked in second position 502: 601-602, 603-604.

In second position 502, a fluid in holding line 211 or holding line 221, which has been pushed into flow line 256, can be pushed by first pump 202 or second pump 204, respectively, through the second multi-port valve 500. The fluid enters at port 603 and exits at port 604 to be introduced into flow cell 104 via flow line 252. Typically, the fluid will be a sample or analyte.

As per multi-port valve 300, multi-port valve 500 can have different configurations such that there are less than the described four channels. The exact configuration of the multi-port valve 300, 500 does not matter as long as they each have a first position and second position in which the flow lines are connected in fluid flow communication as described above.

Figure 7A:
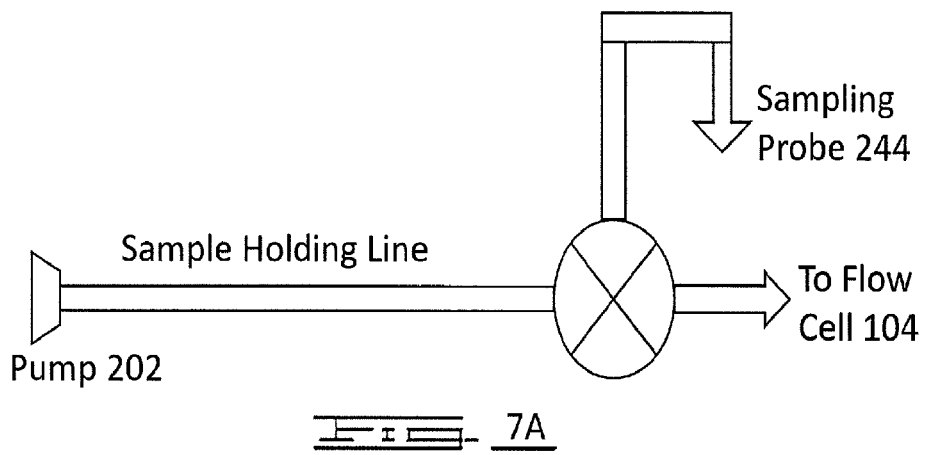
FIGS. 7A through 7E depict in a simplified manner the flow system and generation of a two component gradient.
Figure 7B:
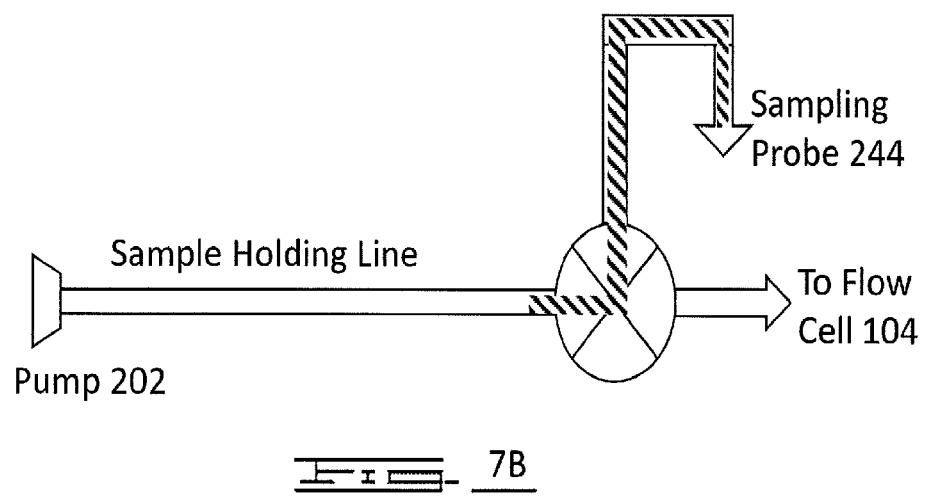
Figure 7C:
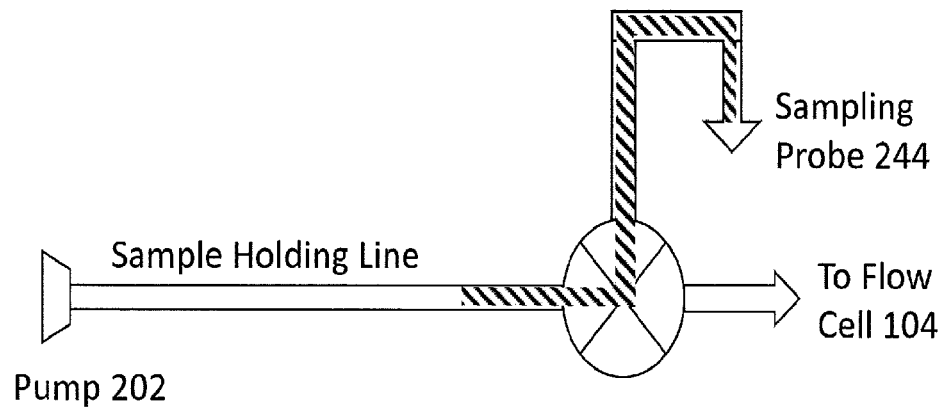
Figure 7D:
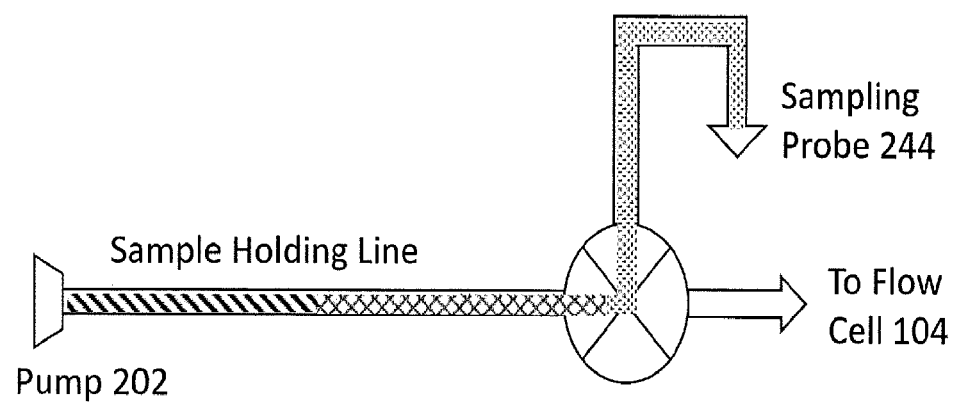
Figure 7E:
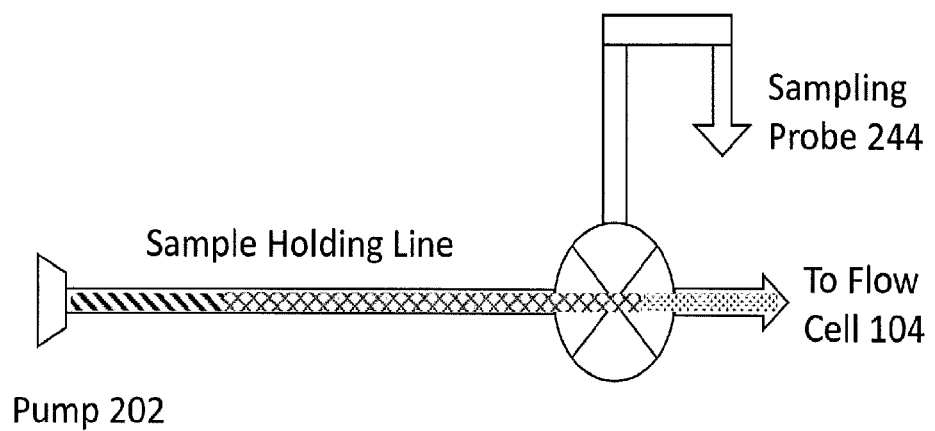

FIGS. 7A-7E provide a simplified view of fluid delivery system 102. The method provided herein provides improved dispersion gradients by using a probe 244 to pull both samples into a sample holding line 213 and subsequently pushing the resulting dispersion gradient through to the SPR flow cell 104 containing the SPR sensing region for SPR binding analysis. Thus, the method prepares a concentration gradient by pulling a first sample into a sample holding line (FIG. 7B) followed by pulling a second sample into the same holding line (FIGS. 7C and 7D). Preferably, prior to pulling the first sample into the holding line an air bubble will be aspirated into the sample holding line. The two samples are in immediate contact with one another and immediately begin to disperse into each other (FIG. 7D). Thus, the dispersion of one sample into the other produces a dispersion gradient for each of the samples. As depicted in FIG. 7E, immediately after pulling the second sample into the sample holding line, the resulting dispersion gradient is pushed to the SPR flow cell containing the sensing region. Thus, the improved method for preparing dispersion gradients utilizes two steps of pulling a sample containing buffer and/or analyte into the sample holding line followed by pushing the resulting dispersion gradient through a flow cell conduit to the SPR flow cell 104 in a single step. The method is also referred to herein as a pull-pull-push method for preparing dispersion gradients. Note: while the discussion provided herein focuses on a two sample dispersion gradient, additional samples may be pulled into the sample holding line forming additional dispersion gradients in a single volume prior to pushing the prepared dispersion gradients to the SPR flow cell 104.

Typically, the volume of each sample pulled into the sample holding line will be between about 10 and 500 μl. The aspiration rate, i.e. the rate at which the sample is pulled into the sample holding line will typically be about 250 μl/minute but may range from about 50 μl/min to about 600 μl/min. The subsequent push of the dispersion gradient formed by combining the two or more components will typically occur at an injection flow rate about 10 μl/min to about 200 μl/min. The total sample volume of the resulting dispersion gradient is limited by the size of the sample holding line. The samples may be combined in a 1:1 ratio or other ratio suitable for the analytes being tested.

The above described pull-pull-push method for forming a dispersion gradient may be used to prepare a bulk refractive index solution of a single analyte in the form of a dispersion gradient and to prepare dispersion gradients of one or more analytes suitable for carrying out competitive binding analysis.

Various binding interaction models can be used in conjunction with the dispersion methods described herein. For example, a simple 1:1 pseudo-first-order kinetic interaction model may be utilized. This model is composed of a differential equation that describes the change in the concentration of affinity complexes (dR/dt) at a sensing region.

$$\frac{dR}{dt} = k_a C(R_{max} - R) - k_d R$$

where
R=biosensor response (response units (RU)),
$R_{max}$=maximum response expected if all ligand sites are occupied (RU)
C=time varying concentration of the analyte at the sensing surface (M)
$k_a$=association rate constant ($m^{-1} s^{-1}$)
$k_d$=dissociation rate constant ($s^{-1}$).
Those skilled in the art will be familiar with other binding interaction models which may be used to determine the binding interaction parameters of interest for the specific analyte/ligand combination.

As is apparent in the above interaction models, analysis of binding interactions requires knowledge of the concentration of each analyte at a given time during the sample injection. Because of the complexities of the sample loading mechanism and the pull-pull-push nature of dispersion gradient injected through the SPR cell 104, an exact mathematical model of the gradient's concentration profile may be impossible to develop. To overcome the difficulty in determining the precise analyte concentration at a given point in time, the present method provides for the generation of an estimated concentration profile.

The generation of the estimated concentration profile utilizes equivalent volumes and flow rates of a liquid sample that will produce a bulk refractive index change at the SPR sensing cell. This bulk refractive index solution does not interact with immobilized ligands used within the SPR sensing region. Accordingly, the bulk refractive index solution provides a direct relationship between observed response and gradient concentration. To perform binding analysis, the concentration profile measured from the bulk refractive index liquid is then used as the concentration term in the binding equations.

In one embodiment, the liquid sample used to produce the bulk refractive index change at the SPR sensing cell will be gradient formed by mixing a buffer with sucrose. Assuming equal volumes of buffer and sucrose, the resulting concentration profile of a gradient formed by dispersion of sucrose in a buffer will depend upon the order of loading the buffer and sucrose solutions in the sample holding line.

Figure 8:
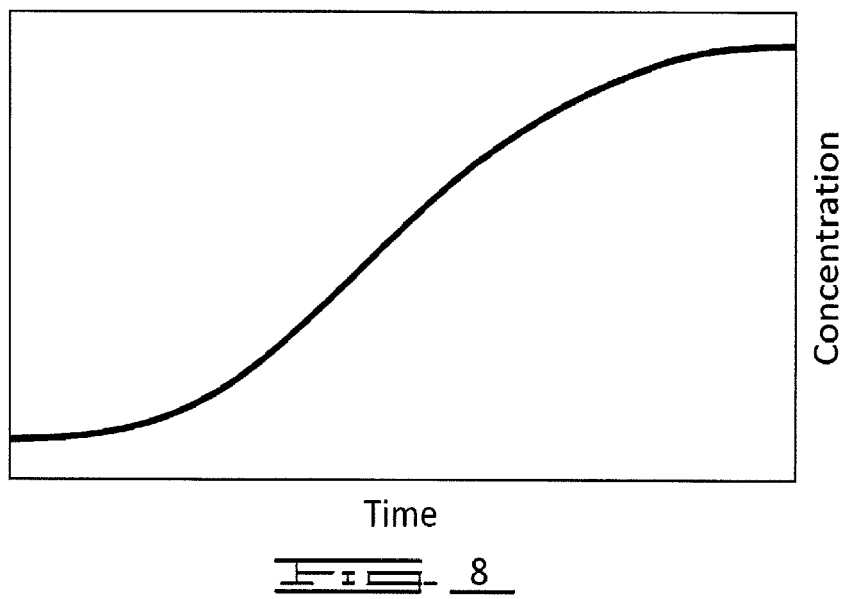
FIG. 8 depicts a graph representative of a gradient formed according to the current method by combining sucrose with a buffer in a 1:1 ratio wherein the sucrose is aspirated into the sample holding line first.
Figure 9:
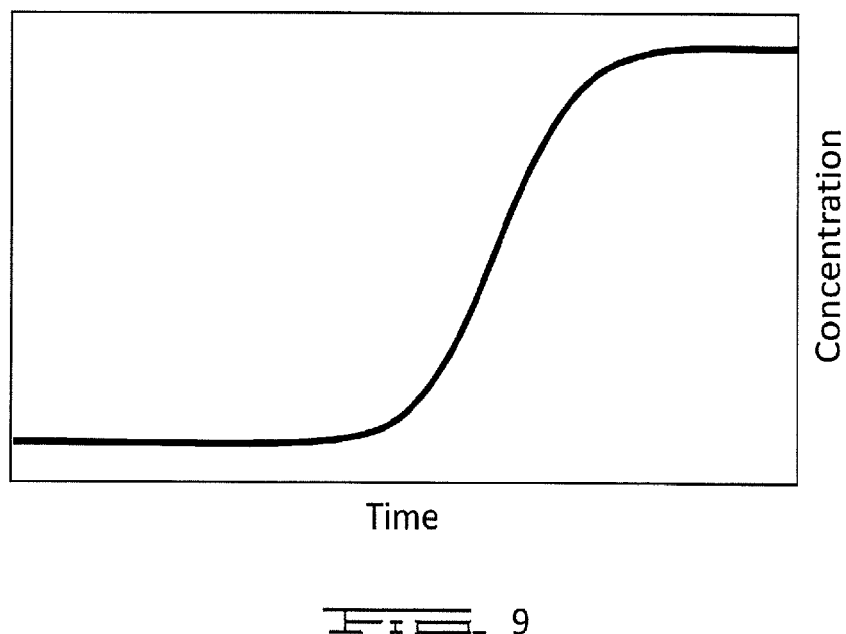
FIG. 9 depicts a graph representative of a gradient formed by the prior art method by combining sucrose with a buffer in a 1:1 ratio.
Figure 10:
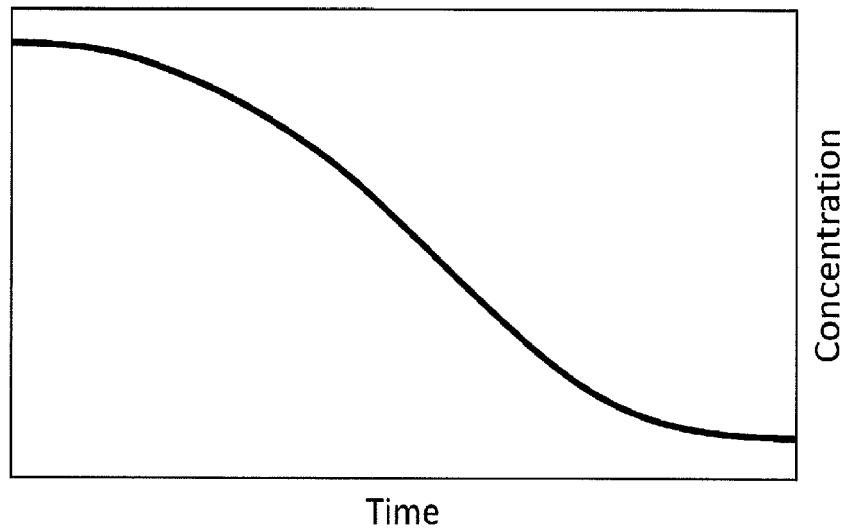
FIG. 10 depicts a graph representative of a gradient formed according to the current method by combining sucrose with a buffer in a 1:1 ratio wherein the sucrose is aspirated into the sample holding line last.

FIG. 8 reflects a concentration profile resulting from the initial aspiration of sucrose into the sample holding line followed by aspiration of buffer. FIG. 10 reflects the concentration profile resulting from the initial aspiration of buffer into the sample holding line followed by aspiration of the sucrose solution. As noted above, the sample load direction is the opposite of the sample injection direction across the SPR sensing cell. FIG. 9 depicts a concentration profile prepared according to prior art methods wherein a sample loop is initially filled with buffer and a sample of sucrose is pulled into a sample holding line. Subsequently, the sucrose is forced into the buffer within the sample loop to create a dispersion gradient and then transported to the SPR cell housing the sensing region.

In contrast to the prior art method for preparing dispersion gradients, i.e. pushing an analyte or sample into a second analyte or buffer to form the dispersion gradient, the present method immediately forms a dispersion gradient upon aspiration of both components into the sample holding line. Thus, the disclosed method can be described as a pull-pull-push of the dispersion gradient. Specifically, the current method provides for pulling of the first sample into the sample holding line followed by pulling of the second sample into the sample holding line. Finally, the method then pushes the resulting dispersion gradient to the SPR cell 104 housing the SPR sensing region. Additional samples may be pulled into the sample holding line prior to pushing the resulting gradient(s) to the SPR cell 104.

As demonstrated by the tables of FIGS. 8-9, the present method alters the slope of the resulting concentration profile for a dispersion gradient of sucrose. As discussed above, the concentration profile of FIG. 9 resulted from the conventional pushing of sucrose into a buffer and determining the concentration profile of the resulting dispersion gradient. The profile of FIG. 9 reflects an initial zero concentration of sucrose in the sample passing through the SPR cell. The concentration of sucrose reflected by FIG. 9 remains zero for a significant time period. When a slope finally appears reflecting passage of sucrose through the SPR cell, the slope is steep and transitions quickly to the high concentration of sucrose. As a result, the concentration profile provides a limited number of data points for use in the binding interaction model equations. In contrast, the concentration profile resulting from a sucrose dispersion gradient, i.e. a bulk refraction index solution, prepared according to the present method provides a significant increase in available data points for use in the binding interaction model equations. Thus, the change in slope reflected by FIG. 8 indicates a longer transition period from low concentration to high concentration, thereby increasing the number of SPR measuring points and improving resolution.

The improvement provided to the concentration profile by the pull-pull-push dispersion gradient method is also found in the subsequent binding interaction profiles as the improved dispersion gradients prepared by the pull-pull-push method will also provide improved resolution during competitive binding analysis. Additionally, the overall time for performing tests will be decreased by eliminating the need to pre-fill the sample loop with buffer or the second analyte. Instead, the present method simply requires aspirating, i.e. pulling, of the samples containing analyte of interest directly into the sample holding line and subsequently pushing the resulting dispersion gradient through to the SPR cell.

Figure 11:
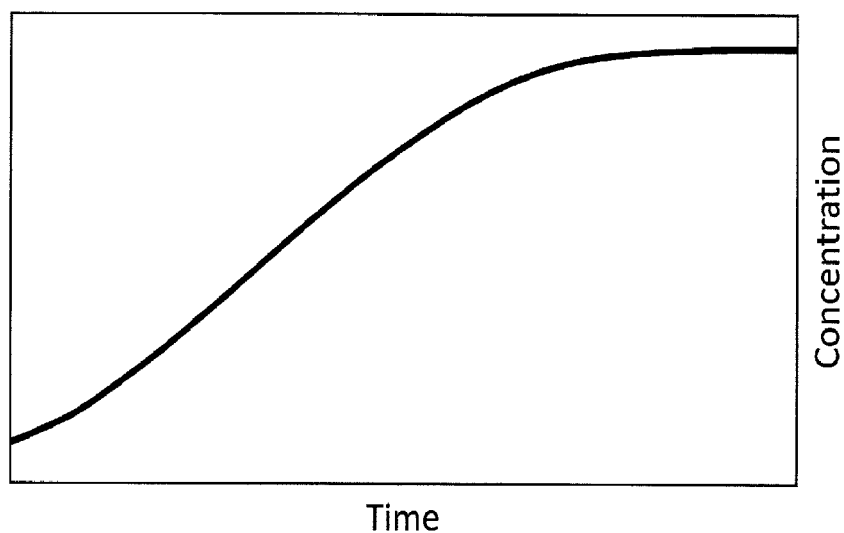
FIG. 11 depicts a graph representative of a gradient formed according to the present method by combining sucrose with a buffer in a ratio of 2:1.
Figure 12:
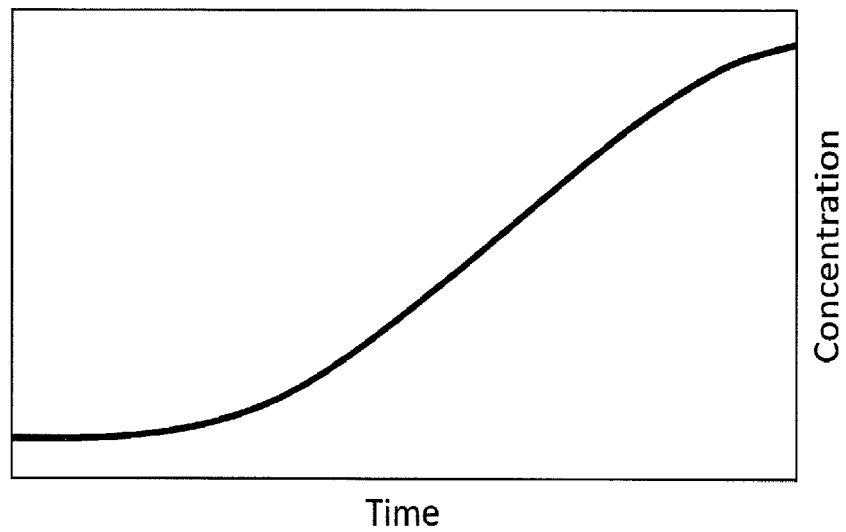
FIG. 12 depicts a graph representative of a gradient formed according to the present method by combining sucrose with a buffer in a ratio of 1:2.

FIGS. 11 and 12 provides concentration profiles for different ratios of buffer and sucrose. In FIG. 11, the graph reflects a concentration profile for a 2:1 ratio of sucrose solution to buffer solution with the sucrose solution aspirated first into the sample holding line. FIG. 12 reflects a concentration profile for 1:2 ratio of sucrose solution to buffer solution with the sucrose solution aspirated first into the sample holding line.

Figure 13:
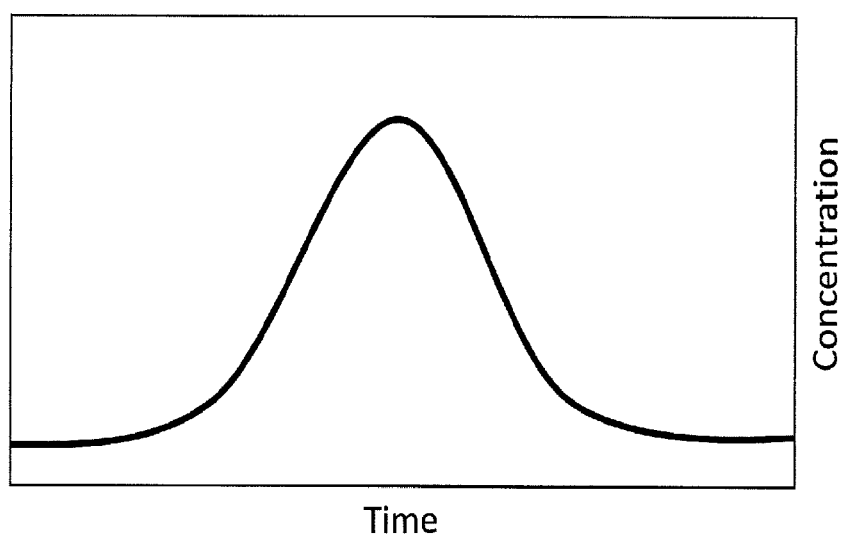
FIG. 13 is a graph representative of a gradient formed by first aspirating buffer followed by an analyte of interest and finally followed by additional buffer.

FIG. 13 reflects another option provided by the current method. FIG. 13 depicts the concentration profile when the sample holding line has been loaded with three samples. In this instance, the sample holding line has been loaded with a sample containing only buffer followed by a sample containing a sucrose solution and followed finally a sample containing only buffer. Thus, as discussed above, the number of species loaded into sampling holding line will be limited solely by the volume of the holding line. However, in most cases two or three target analytes will be the limit for analysis.

The procedure for filling the sample holding line when preparing the bulk refractive index solution and subsequent analyte dispersion gradients will normally use the following steps:

1. Syringe pump 202 aspirates an air bubble segment to separate the system buffer from the first sample. The first sample is loaded into the system by aspirating with pump 202 via the path Sample Racks 246→Probe 244→Line 242→Line 256→Line 213.
2. After aspirating the desired volume of first sample, the autosampler probe is moved to the sample rack position containing the second sample without introducing an air bubble or any other separation between the first and second sample. The second sample is then aspirated along the same path as the first sample.
3. After aspirating the desired volume of the second sample, the autosampler probe is moved to a home position such that the tip is exposed to the local atmosphere. Pump 202 aspirates an additional volume of air such that the first and second sample are moved into position to be injected into the flow cell—that is, up to the point where only a small safety volume (~5 ul) remains in Line 242, while the balance is pulled into Line 256 & Line 213
4. At this point the first and second samples have dispersed into each other and a gradient is formed.
5. The single gradient segment is now injected into the flow cell by changing the position of the 2/4 valve 500 so that pump 202 may dispense the gradient sample into the flow cell via path Line 213→Line 256→Line 252→Flow Cell 104. As noted above, pump 202, the sample holding line and flow cell line to flow cell 104 are shown in simplified form in FIGS. 7A-7E.

The volumes and flow rates used in these steps are discussed above.

If more than two samples are to be loaded into the sample holding line, the above pull-pull-push procedure is used as described. However, after loading the second sample, the auto-sampler will move to the next sample position and provide for aspiration, i.e. pulling, of an additional sample into the sample holding line.

As discussed above, use of the foregoing method to prepare bulk refractive index solutions will provide improved concentration profiles suitable for use as reference points for model fitting of subsequent analyte dispersion gradients. The method disclosed herein is particularly suited for competitive binding interaction analysis.

The method for preparing dispersion gradients of samples containing analytes for binding competition analysis follows the same pull-pull-push as discussed above. The method of carrying out the competitive analysis will be discussed with reference to FIGS. 14-18.

Figure 14:
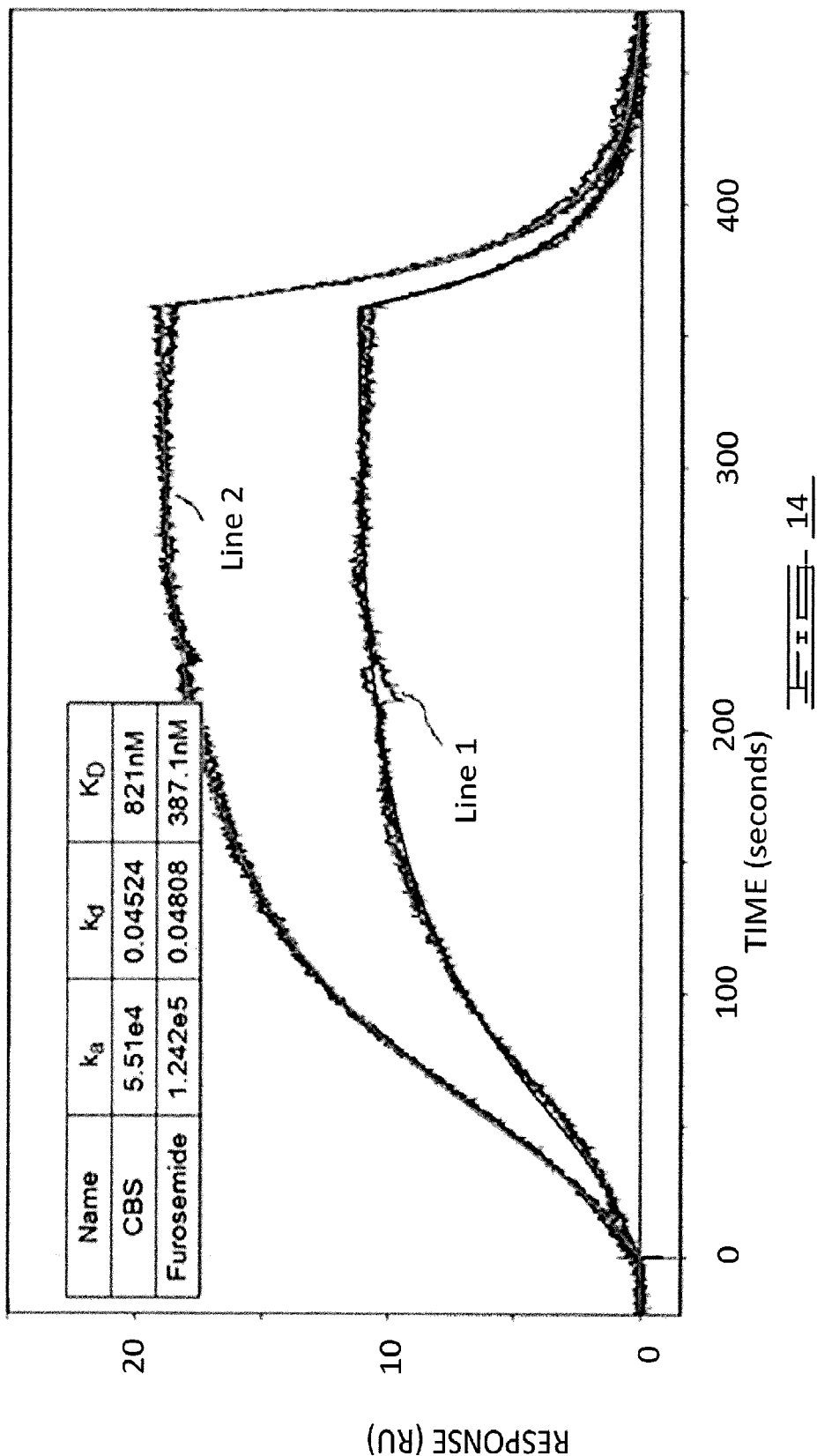
FIG. 14 depicts the binding response curves for injections of dispersion gradients of CBS and Furosemide prepared according to the method of the present invention wherein the analyte is aspirated first into the sample holding line followed by aspiration of the buffer.
Figure 15:
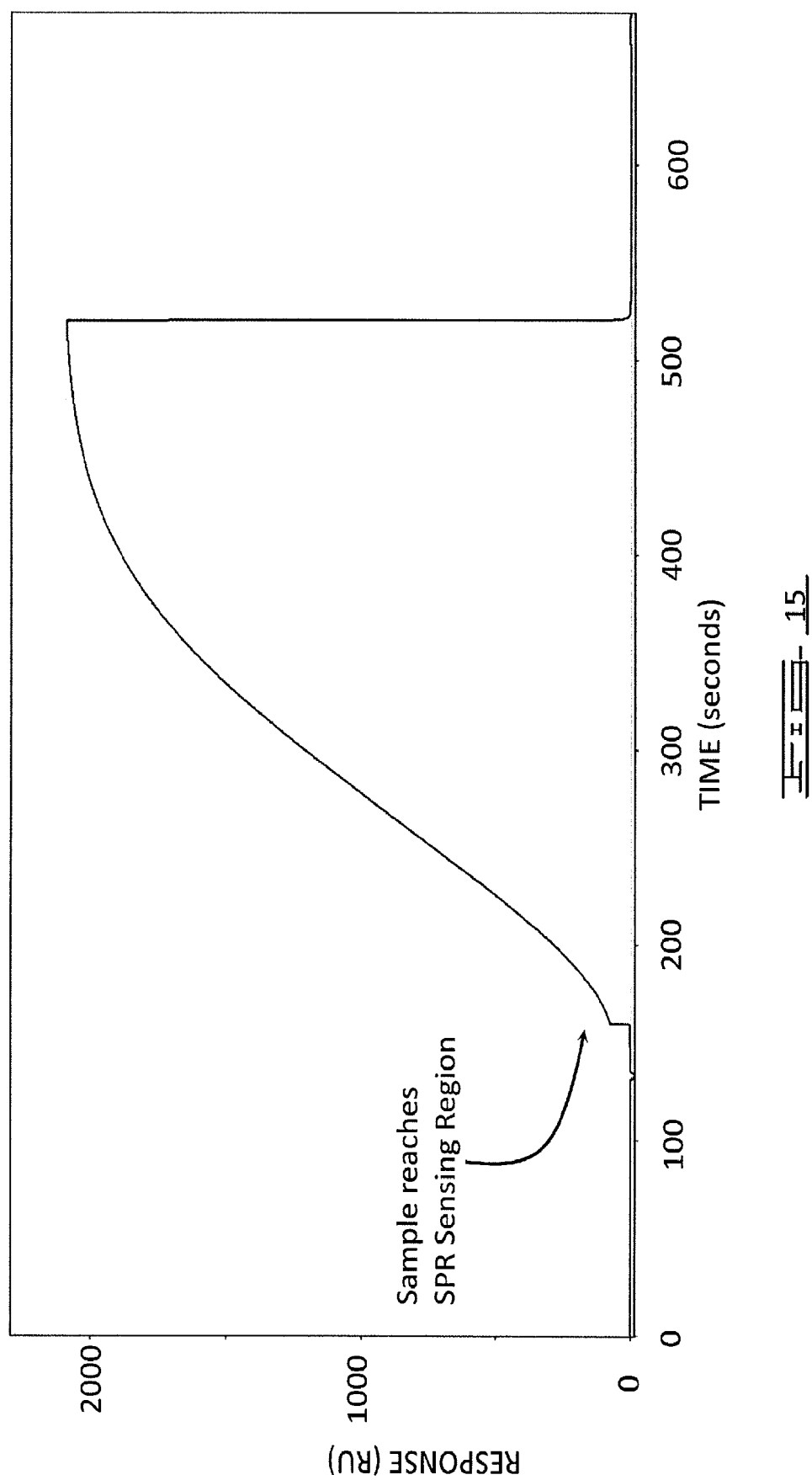
FIG. 15 is a concentration profile of sucrose in buffer used to provide the concentration approximation in the binding models applied in FIG. 14.

FIG. 14, line 1 reflects the binding interaction response of 4-carboxy-benzenesulfonamide (CBS) and line 2 reflects the binding interaction response of Furosemide. The binding interaction analysis was carried out using a SPR cell having a sensing region wherein the bound ligand is Carbonic anhydrase II enzyme immobilized on the surface of the biosensor via amine coupling to ~6500 RU. The dispersion gradient of Furosemide was prepared using 200 µl of a 1 µM solution of Furosemide and 100 µl of phosphate buffered saline (buffer). According to the method described above, the dispersion gradient was prepared by initially aspirating, pulling, the Furosemide into the sample holding line followed by pulling the buffer into the sample holding line. The resulting dispersion gradient of Furosemide in buffer was immediately injected, pushed, at a flow rate of 50 µl/min through the SPR sensing region containing the bound ligand. The dispersion gradient of CBS was prepared using 200 µl of a 2 µM of CBS and 100 µl of buffer. The dispersion gradient of CBS in buffer was prepared by initially aspirating the CBS into the sample holding line followed by pulling the buffer into the sample holding line. The resulting dispersion gradient was immediately injected at a flow rate of 50 µl/min through the SPR sensing region containing the bound ligand.

A bulk refractive index solution of sucrose (1.5% w/v) in PBS was prepared and injected using the same technique in order to provide a concentration profile curve as depicted in FIG. 12. As discussed above, the concentration profile curve is used in the fitting of a binding interaction model to the binding result curves produced by the injection of the dispersion gradients through the SPR cell. As known to those skilled in the art, the fitting of the binding interaction model to the binding response curve allows for determination of $k_a$, $k_d$ and $K_D$. Thus, FIG. 15 demonstrates the effectiveness of preparing dispersion gradients according to the pull-pull-push method disclosed herein.

Having confirmed the ability to prepare dispersion gradients of samples containing analytes suitable for producing binding interaction curves, the present method enables a fast, low cost method for performing competitive binding analysis. The method for performing competitive binding analysis is suitable for determining whether one analyte blocks the binding of another analyte to a target ligand or increases the binding capabilities of an analyte.

Figure 16:
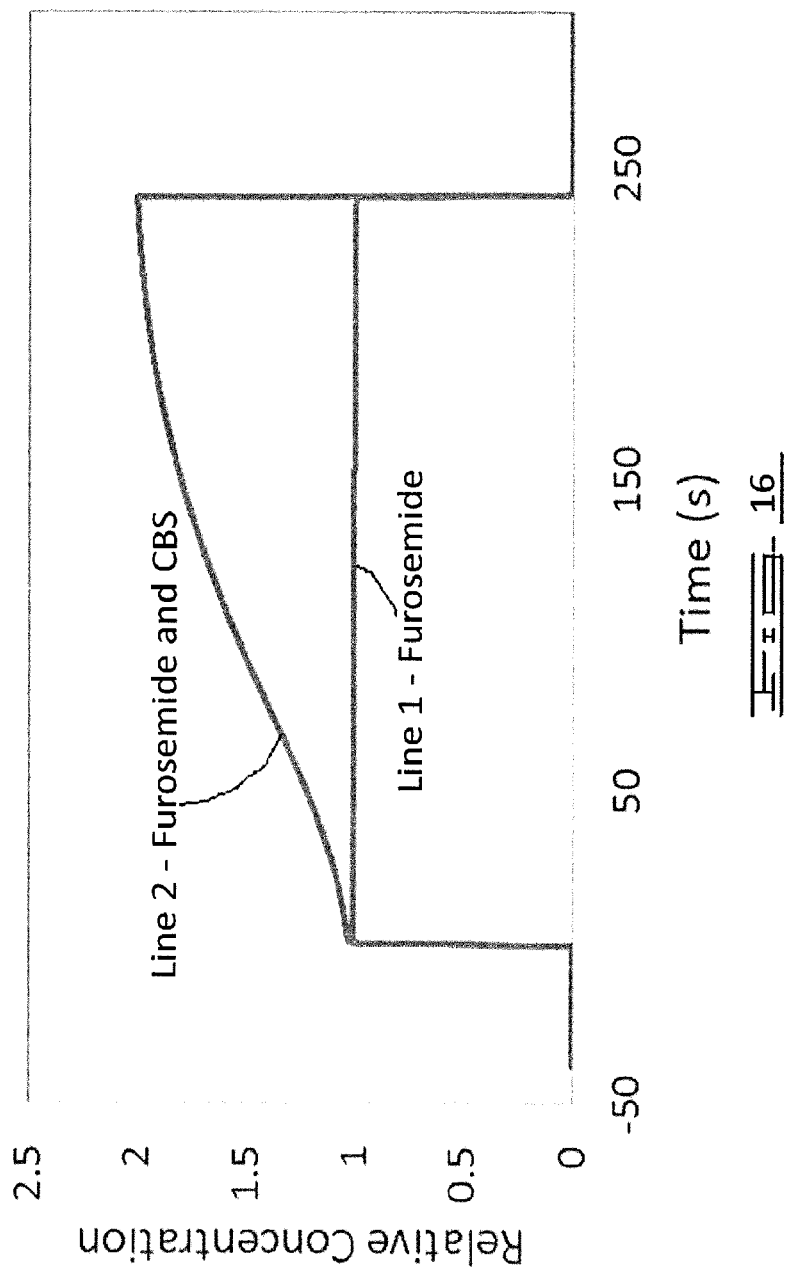
FIG. 16 is the relative concentrations of CBS and Furosemide used in a binding interaction competitive analysis of the two analytes.
Figure 17:
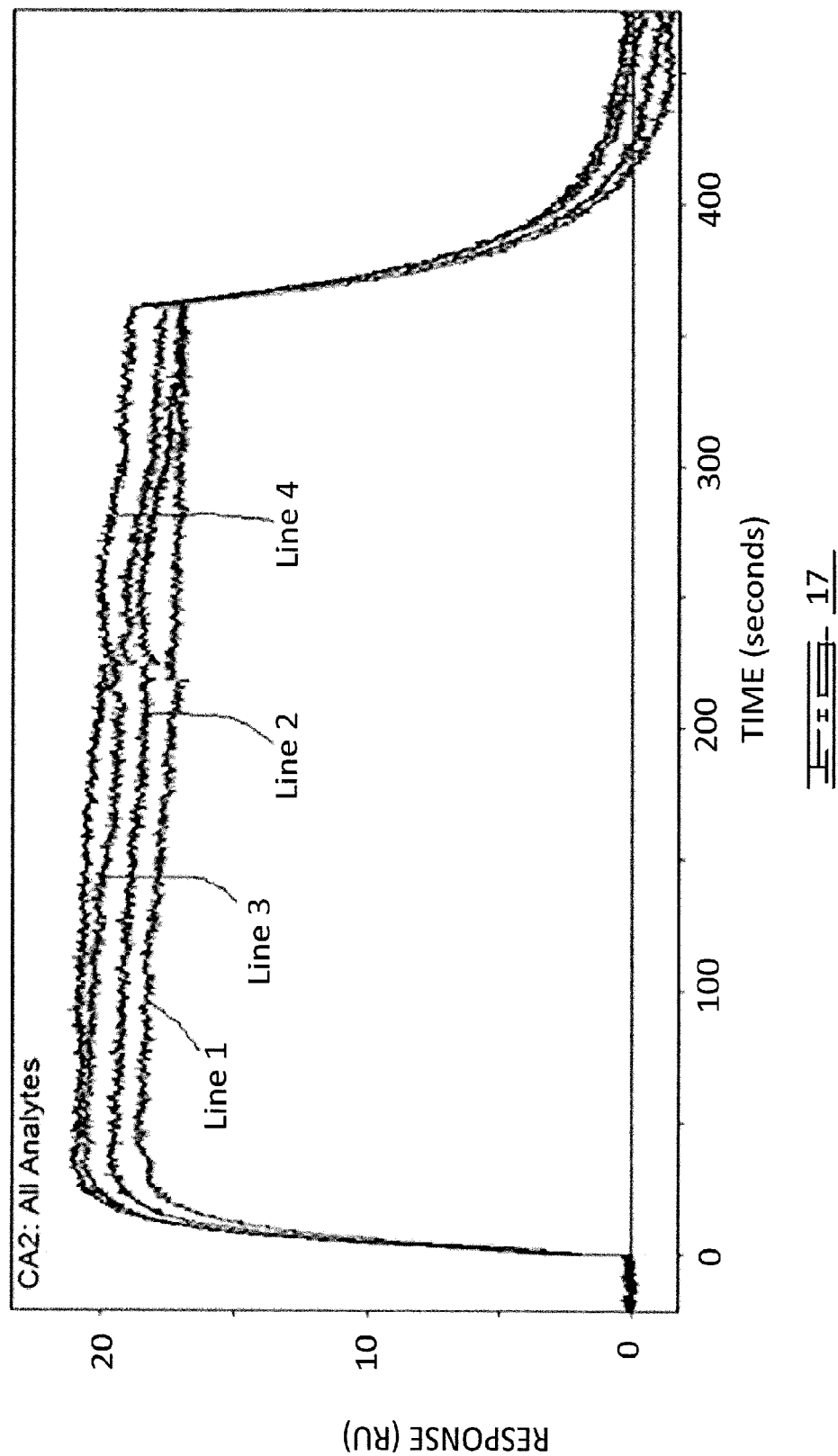
FIG. 17 depicts the binding interaction analysis generated by analyte injections in a binding interaction competitive analysis.
Figure 18:
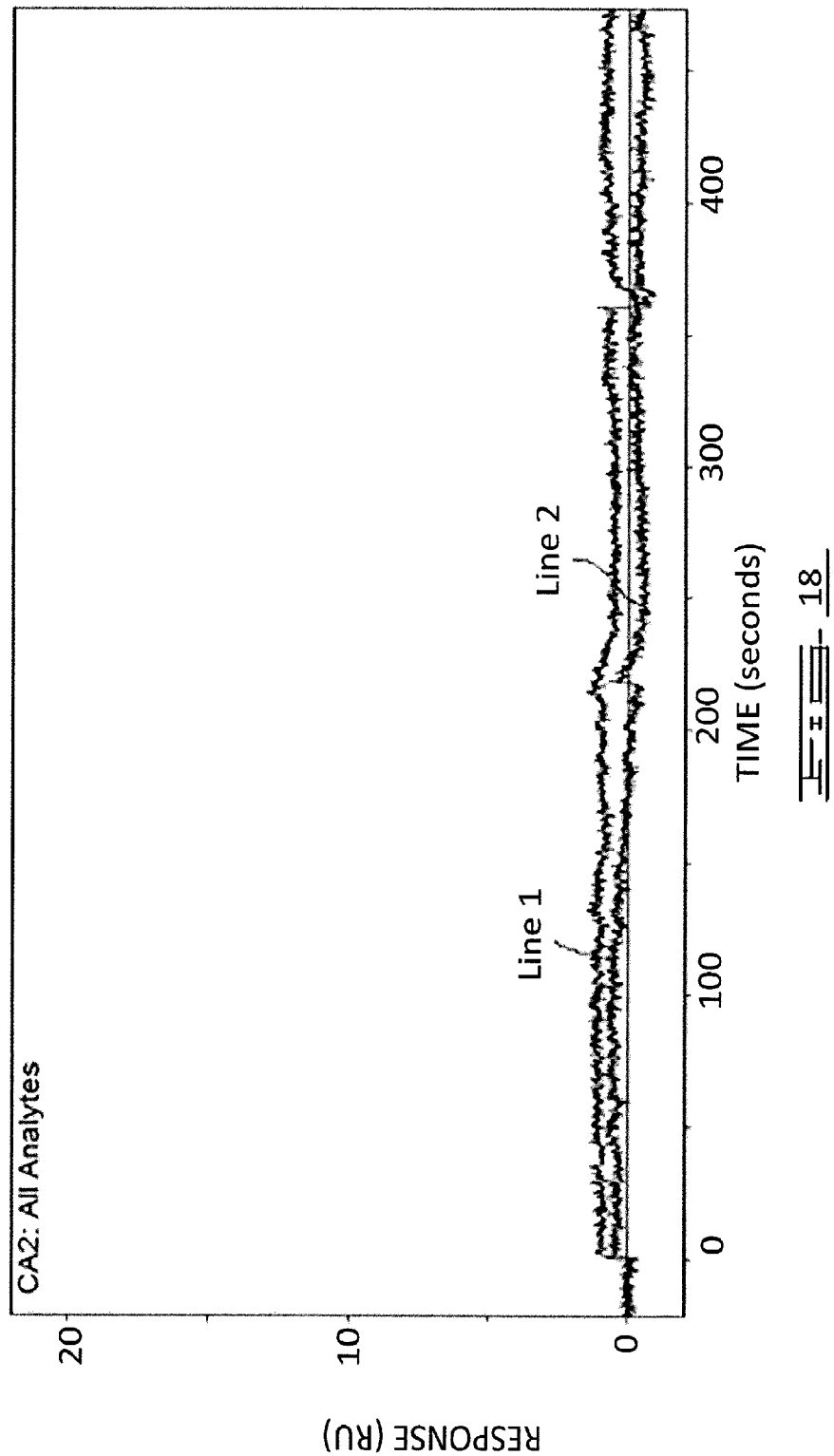
FIG. 18 depicts the resulting binding of CBS in the presence of Furosemide.

FIGS. 16-18 will be referenced with regard to the method of determining binding competitive analysis. FIG. 16 reflects the relative concentrations of analyte when performing a binding competition analysis. The analytes used in the binding competition analysis are Furosemide and CBS. The analysis is designed to determine if CBS will bind to the ligand when Furosemide is present.

With reference to FIG. 16, the relative concentration of Furosemide, Line 1, is unchanged during the competitive analysis. In contrast, the relative concentration of CBS will increase as a dispersion gradient during the competitive analysis.

The binding response curves of FIG. 17 were prepared by injecting two samples. The sample injected was prepared using the pull-pull-push method by aspirating a first volume of Furosemide followed by aspirating a second volume of Furosemide. The resulting control sample of Furosemide solution was injected through the SPR cell for analysis. The resulting binding interaction curves are identified as Lines 2 and 4 in FIG. 17. This injection of the Furosemide solution is a control injection of the competitor analyte which demonstrates the binding of the competitor analyte to the ligand within the SPR cell. The competitive binding of CBS in the presence of Furosemide will be determined using the next gradient dispersion injection. As will be discussed in more detail below, the control injection of the competitor analyte is optional.

In one preferred embodiment, the second gradient dispersion injection was prepared by aspirating a first sample of the mixture of CBS/Furosemide followed by aspirating a sample of Furosemide thereby generating a dispersion gradient between the two samples. The order of the aspiration in the second injection ensures that the ligand will see Furosemide prior to seeing CBS. The binding interaction curves associated with the second gradient dispersion are identified as Lines 1 and 3. Under these conditions, if CBS were to bind to the ligand during the analysis, one would expect a binding response curve to increase as the concentration of CBS increases. The injections were repeated to demonstrate reproducibility of the method. In an alternative embodiment, the second injection alone will suffice to determine qualitatively the binding of CBS in the presence of Furosemide.

To determine the binding interaction response of CBS in the second injection, one subtracts the binding interaction curves associated only with Furosemide from the binding interaction curves associated with the Furosemide with CBS/Furosemide injection. As reflected by FIG. 18, the subtracted curves, lines 1 and 2, indicate that no binding of CBS occurs under these conditions. The result is expected as these molecules are both sulfonamides and derive their affinity from the sulfonamide functional group present on both molecules.

In the alternative embodiment, where a control injection of the competitor is not used, one may perform qualitative analysis of the binding interaction curve generated by the gradient dispersion generated by pulling the sample containing analyte plus competitor followed by pulling the sample of only competitor and pushing the resulting gradient through the SPR cell. With reference to FIG. 17, lines 1 and 3 reflect the binding interaction curves generated by such a dispersion gradient. The initial binding interaction of these curves is attributable to only the competitor, i.e. Furosemide. Qualitative analysis can be carried out by observing the later part of the binding interactive curve. If the curve progresses upward then the tested analyte can be assumed to contribute to the binding interaction and thus positively competes with the competitor. However, if as depicted in FIG. 17, the curve remains substantially steady state for the period of time of the dispersion gradient passing through the SPR cell, the tested analyte, e.g. CBS, does not compete and does not contribute to the binding interaction. Thus, one can qualitatively conclude that CBS would not bind to the ligand in the presence of Furosemide. As discussed above, this conclusion is supported by FIG. 18.

In yet another embodiment, the dispersion gradient may be prepared by pulling the target analyte followed by pulling the competitor and pushing the resulting gradient to the SPR cell for analysis. Under these conditions, one will preferably perform the control injection of only the competitor in order to establish a baseline binding interaction curve for the competitor analyte.

Thus, the improved method for producing a dispersion gradient is particularly suited for screening molecules for competition against known binders. The competition analysis may demonstrate blocking of one compound by another or enhanced binding of one compound in the presence of the control compound may indicate allosteric or cooperative binding or affinities greater than the control itself. The ability to screen compounds or other analytes for mechanism characteristics would be valuable for drug discovery programs.

The following is a concise summary of the method for performing the competitive binding analysis. The volumes and flow rates are described above. In general, each sample pulled into the sample holding line will be between about 10 and 500 µl. The aspiration rate, i.e. the rate at which the sample is pulled into the sample holding line will typically be about 250 µl/minute but may range from about 50 µl/min to about 600 µl/min. The subsequent push of the dispersion gradient formed by combining the two or more components will typically occur at an injection flow rate about 10 µl/min to about 200 µl/min. This method uses an SPR cell containing an appropriately immobilized ligand wherein the ligand has been selected for its ability to bind the analytes being tested. Use of the disclosed method permits rapid screening of a plurality of competitor species.

Step 1: Optionally prepare a control sample containing only the competitor analyte. Perform SPR analysis to determine the binding interaction of the competitor analyte with the ligand bound in the SPR cell by pulling a first sample of the competitor analyte into the sample holding line, pulling a second sample of the competitor analyte into the sample holding line and pushing the resulting solution through the SPR cell. This approach ensure consistency in the injections of the competitor and the target analyte when generating the. control binding response curve Step 2: Preparing and analyzing a binding competitive analysis dispersion gradient of the target analyte and competitor by pulling a prepared sample containing both the target analyte and competitor into the sample holding line, pulling a sample containing the competitor into the target holding line and pushing the resulting dispersion gradient through the SPR cell for analysis by the SPR sensor. A binding response curve is recorded of the response of the SPR sensor to the competitor and competitor+analyte dispersion gradient injection. This is the analyte binding response curve.

Step 2—Alternative: A dispersion gradient injection is performed where the first sample pulled contains only the analyte species of interest. The second sample pulled contains only the competitor analyte. A binding response curve is recorded of the response of the SPR sensor to the resulting dispersion gradient injection.

Step 4: The control binding response curve is subtracted from the analyte binding response curve to produce a referenced analyte binding response curve.

Step 5: Determination of the effect of analyte binding in the presence of competitor species. This may be done by testing for binding response to exceed some baseline threshold in the referenced analyte binding response curve, where exceeding the threshold indicates analyte binding in the presence of competitor, and not exceeding the threshold indicates no analyte binding in the presence of the competitor.

Other embodiments of the present invention will be apparent to one skilled in the art. As such, the foregoing description merely enables and describes the general uses and methods of the present invention. Accordingly, the following claims define the true scope of the present invention.

The invention claimed is:

1. A method for performing competitive binding analysis of two analytes comprising:
  preparing a control sample of a first analyte by pulling a first sample of said first analyte into a sample holding line, pulling a second sample of said first analyte into said sample holding line;
  injecting said control sample through an SPR sensor, said SPR sensor including a bound ligand;
  measuring a binding interaction of the first analyte in the control with said ligand using SPR analysis to generate a binding interaction curve;
  preparing a binding competitive analysis dispersion gradient by pulling a sample comprising the first analyte and a second analyte into the sample holding line, followed by pulling a sample of the first analyte into the sample holding line thereby forming the binding competitive analysis dispersion gradient;
  pushing the resulting binding competitive analysis dispersion gradient through said SPR sensor;

measuring a binding interaction of the binding competitive analysis dispersion gradient with said ligand to generating a binding interaction curve;

subtracting the binding interaction curve generated by the control sample from the binding interaction curve generated by the binding competitive analysis dispersion gradient to produce an analyte binding response curve for the second analyte to the ligand in the presence of the first analyte.

2. The method of claim 1 wherein the volume of each sample pulled into the sample holding line will be between about 10 and 500 µl.

3. The method of claim 1 wherein the rate at which each sample is pulled into the sample holding line is from about 50 µl/min to about 600 µl/min.

4. The method of claim 1 wherein the rate at which each sample is pulled into the sample holding line is about 250 µl/min.

5. The method of claim 1 wherein the pushing of the binding competitive analysis dispersion gradient takes place at a flow rate of about 10 µl/min to about 200 µl/min.

6. The method of claim 1 wherein the pushing of the control takes place at a flow rate of about 10 µl/min to about 200 µl/min.

\* \* \* \* \*